(12) United States Patent
Ye et al.

(10) Patent No.: US 8,541,525 B2
(45) Date of Patent: Sep. 24, 2013

(54) COMPOUND COMPRISING PHENYL PYRIDINE UNITS

(75) Inventors: Qing Ye, Los Gatos, CA (US); Jie Liu, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 132 days.

(21) Appl. No.: 13/056,539

(22) PCT Filed: Jul. 9, 2009

(86) PCT No.: PCT/US2009/049990
§ 371 (c)(1), (2), (4) Date: Jan. 28, 2011

(87) PCT Pub. No.: WO2010/016991
PCT Pub. Date: Feb. 11, 2010

(65) Prior Publication Data
US 2011/0207877 A1    Aug. 25, 2011

(30) Foreign Application Priority Data
Aug. 7, 2008  (CN) .......................... 2008 10 129825

(51) Int. Cl.
*C08F 30/06* (2006.01)
(52) U.S. Cl.
USPC ............................ 526/239; 428/690; 524/547
(58) Field of Classification Search
USPC ................. 428/690; 524/547; 526/239, 258, 526/265; 546/13
See application file for complete search history.

(56) References Cited

U.S. PATENT DOCUMENTS 8,025,987 B2 * 9/2011 Takahashi et al. ............ 428/690
2009/0208776 A1 * 8/2009 Liu et al. ...................... 428/690

FOREIGN PATENT DOCUMENTS
WO    2006/135076 A1    12/2006

OTHER PUBLICATIONS

International Search Report and Written Opinion, Oct. 19, 2009.
Tanaka, Takeda, Chiba, Watanabe, Kido: "Novel Electron Transport Material containing Boron Atom with a High Triplett Excited Energy Level" Chemistry Letters vol. 36, 2007.

* cited by examiner

*Primary Examiner* — David W Wu
*Assistant Examiner* — Marie Reddick
(74) *Attorney, Agent, or Firm* — Global Patent Operation

(57) ABSTRACT

Polymers comprising structural units derived from compounds of formula I may be used in optoelectronic devices

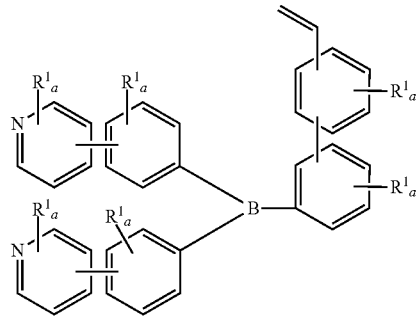

wherein
R1 is independently at each occurrence a C1-C20 aliphatic radical, a C3-C20 aromatic radical, or a C3-C20 cycloaliphatic radical; and a is independently at each occurrence 0, or an integer ranging from 1 to 4.

12 Claims, No Drawings

COMPOUND COMPRISING PHENYL PYRIDINE UNITS

BACKGROUND

The invention relates generally to compounds, and particularly to compounds comprising phenyl pyridine units, polymers comprising structural units derived from the compounds and optoelectronic devices using the same.

Optoelectronic devices, e.g. Organic Light Emitting Devices (OLEDs), which make use of thin film materials that emit light when subjected to a voltage bias, are expected to become an increasingly popular form of flat panel display technology. This is because OLEDs have a wide variety of potential applications, including cell phones, personal digital assistants (PDAs), computer displays, informational displays in vehicles, television monitors, as well as light sources for general illumination. Due to their bright colors, wide viewing angle, compatibility with full motion video, broad temperature ranges, thin and conformable form factor, low power requirements and the potential for low cost manufacturing processes, OLEDs are seen as a future replacement technology for cathode ray tubes (CRTs) and liquid crystal displays (LCDs). Due to their high luminous efficiencies, OLEDs are seen as having the potential to replace incandescent, and perhaps even fluorescent, lamps for certain types of applications.

OLEDs possess a sandwiched structure, which consists of one or more organic layers between two opposite electrodes. For instance, multi-layered devices usually comprise at least three layers: a hole injection/transport layer, an emissive layer and an electron transport layer (ETL). Furthermore, it is also preferred that the hole injection/transport layer serves as an electron blocking layer and the ETL as a hole blocking layer. Single-layered OLEDs comprise only one layer of materials between two opposite electrodes.

BRIEF DESCRIPTION

In one aspect, the invention relates to compounds of formula I:

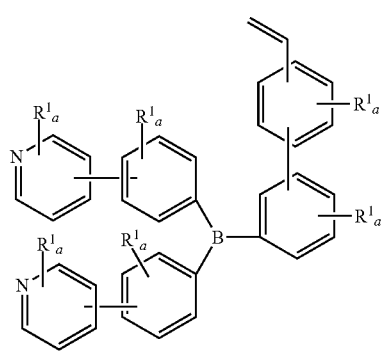

I wherein
$R^1$ is independently at each occurrence a $C_1$-$C_{20}$ aliphatic radical, a $C_3$-$C_{20}$ aromatic radical, or a $C_3$-$C_{20}$ cycloaliphatic radical; and
a is independently at each occurrence 0, or an integer ranging from 1 to 4.

In another aspect, the invention relates to optoelectronic devices comprising at least one compound of formula I and/or polymer comprising structural units derived from the compound, particularly where the polymer is present in an electron-transporting layer.

DETAILED DESCRIPTION

Polymers comprising structural units derived from compounds of formula I have properties useful in optoelectronic devices, e.g., organic light emitting devices (OLEDs), and are particularly well suited for use in electron-transporting layers thereof.

In one embodiment, the present invention relates to compounds of formula II and polymers derived therefrom and optoelectronic devices using the same

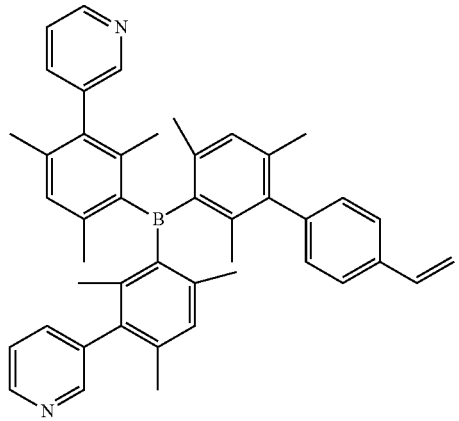

II

The compounds of formula I and II may be prepared by employing Suzuki cross-coupling reactions. The general procedure for Suzuki cross-coupling reactions includes mixing an aryl halide and aryl borate (or boronic acid) in a suitable solvent, in the presence of a base and Pd catalyst. The reaction mixture is heated under an inert atmosphere for a period of time. Suitable solvents include but are not limited to Dioxane, THF, EtOH, toluene and mixtures thereof. Exemplary bases include $Na_2CO_3$, $K_2CO_3$, $Cs_2CO_3$, Potassium phosphate and hydrates thereof. The bases can be added to the reaction as a solid powder or as an aqueous solution. The most commonly used catalysts include $Pd(PPh_3)_4$, or $Pd(OAc)_2$, $Pd(dba)_2$ with the addition of a secondary ligand. Exemplary ligands include dialkylphosphinobiphenyl ligands, such as structures III-VII shown below, in which Cy is cyclohexyl.

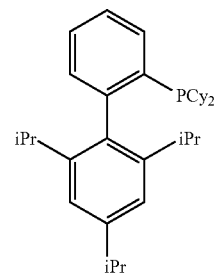

III

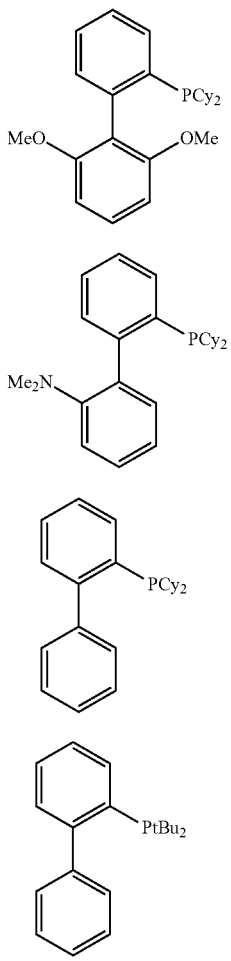

IV

V

VI

VII

Polymers having structural units of formula I or II may additionally include structural units derived from comonomers containing pendant heteroaromatic groups, such as vinylpyridine, vinylcarbazole, vinylphenylcarbazole and vinylphenylpyridine. In particular, structural units of formula VIII, derived from vinylphenylpyridine, may be included.

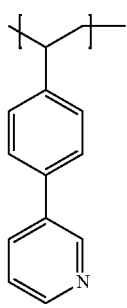

VIII

Other comonomers that may be used include, but are not limited to, (meth)acrylic acid and derivatives thereof, vinyl compounds including vinyl methyl ether, vinyl esters, such as, for example, vinyl acetate and vinyl propionate, vinyl aromatic monomers, such as, for example, styrene and substituted styrenes having one or more alkyl, alkoxy, hydroxy or halo substituent groups attached to the aromatic ring, including, but not limited to, alpha-methyl styrene, p-methyl styrene, 3,5-diethylstyrene, 4-n-propylstyrene, vinyl toluene, alpha-methyl vinyltoluene, vinyl xylene, trimethyl styrene, butyl styrene, t-butyl styrene, chlorostyrene, alpha-chlorostyrene, dichlorostyrene, tetrachloro styrene, bromostyrene, alpha-bromostyrene, dibromostyrene, p-hydroxystyrene, p-acetoxystyrene, methoxystyrene and vinyl-substituted condensed aromatic ring structures, such as, for example, vinyl naphthalene, vinyl anthracene, and maleimide monomers, such as, for example, maleimide, N-alkyl maleimides, N-aryl maleimides and haloaryl substituted maleimides; maleic anhydride.

Any radical polymerization method known in the art can be used in the present application. All monomers were weighed out and dissolved in a vial using minimum amount of solvent and the solution were transferred to a schlenk tube using pipette. Suitable solvents include THF, NMP etc. Some solvent was used to rinse the vial and aid transfer. The radical initiator was added to the schlenk tube via a syringe. The solution was degassed by a freeze-pump-thaw cycle three times and kept sealed under vacuum during the reaction. The schlenk tube was then immersed into a pre-heated oil bath set to 65-180° C. and left to stir. The tube was then removed from the bath and let cool. The polymer was then precipitated into anti-solvent such as ether, hexanes, methanol or acetone. Monomers synthesized in house were used without further purification, as they do not contain any radical inhibitors. All thermal initiators such as AIBN and BPO can be used in. Monomers obtained commercially would be purified through an $AlO_2$ plug to remove radical inhibitors before use.

An optoelectronic device, e.g., an OLED, typically includes in the simplest case, an anode layer and a corresponding cathode layer with an organic electroluminescent layer disposed between said anode and said cathode. When a voltage bias is applied across the electrodes, electrons are injected by the cathode into the electroluminescent layer while electrons are removed from (or "holes" are "injected" into) the electroluminescent layer from the anode. Light emission occurs as holes combine with electrons within the electroluminescent layer to form singlet or triplet excitons, light emission occurring as singlet and/or triplet excitons decay to their ground states via radiative decay.

Other components which may be present in an OLED in addition to the anode, cathode and light emitting material include a hole injection layer, an electron injection layer, and an electron transport layer. The electron transport layer need not be in direct contact with the cathode, and frequently the electron transport layer also serves as a hole blocking layer to prevent holes migrating toward the cathode. Additional components which may be present in an organic light-emitting device include hole transporting layers, hole transporting emission (emitting) layers and electron transporting emission (emitting) layers.

In one embodiment, the OLEDs comprising the organic compounds of the invention may be a fluorescent OLED comprising a singlet emitter. In another embodiment, the OLEDs comprising the organic compounds of the invention may be a phosphorescent OLED comprising at least one triplet emitter. In another embodiment, the OLEDs comprising the organic compounds of the invention comprise at least one singlet emitter and at least one triplet emitter. The OLEDs comprising the organic compounds of the invention may contain one or more, any or a combination of blue, yellow, orange, red phosphorescent dyes, including complexes of transition metals such as Ir, Os and Pt. In particular, electrophosphorescent and electrofluorescent metal complexes, such as those supplied by American Dye Source, Inc., Quebec, Canada may be used. Polymers comprising structural units deriving from compounds of the formula I and II may be part of an emissive layer, or hole transporting layer or electron transporting layer, or electron injection layer of an OLED or any combination thereof.

The organic electroluminescent layer, i.e., the emissive layer, is a layer within an organic light emitting device which when in operation contains a significant concentration of both electrons and holes and provides sites for exciton formation and light emission. A hole injection layer is a layer in contact with the anode which promotes the injection of holes from the anode into the interior layers of the OLED; and an electron injection layer is a layer in contact with the cathode that promotes the injection of electrons from the cathode into the OLED; an electron transport layer is a layer which facilitates conduction of electrons from the cathode and/or the electron injection layer to a charge recombination site. During operation of an organic light emitting device comprising an electron transport layer, the majority of charge carriers (i.e. holes and electrons) present in the electron transport layer are electrons and light emission can occur through recombination of holes and electrons present in the emissive layer. A hole transporting layer is a layer which when the OLED is in operation facilitates conduction of holes from the anode and/or the hole injection layer to charge recombination sites and which need not be in direct contact with the anode. A hole transporting emission layer is a layer in which when the OLED is in operation facilitates the conduction of holes to charge recombination sites, and in which the majority of charge carriers are holes, and in which emission occurs not only through recombination with residual electrons, but also through the transfer of energy from a charge recombination zone elsewhere in the device. An electron transporting emission layer is a layer in which when the OLED is in operation facilitates the conduction of electrons to charge recombination sites, and in which the majority of charge carriers are electrons, and in which emission occurs not only through recombination with residual holes, but also through the transfer of energy from a charge recombination zone elsewhere in the device.

Materials suitable for use as the anode includes materials having a bulk resistivity of preferred about 1000 ohms per square, as measured by a four-point probe technique. Indium tin oxide (ITO) is frequently used as the anode because it is substantially transparent to light transmission and thus facilitates the escape of light emitted from electro-active organic layer. Other materials, which may be utilized as the anode layer, include tin oxide, indium oxide, zinc oxide, indium zinc oxide, zinc indium tin oxide, antimony oxide, and mixtures thereof.

Materials suitable for use as the cathode include general electrical conductors including, but not limited to metals and metal oxides such as ITO etc which can inject negative charge carriers (electrons) into the inner layer(s) of the OLED. Various metals suitable for use as the cathode 20 include K, Li, Na, Cs, Mg, Ca, Sr, Ba, Al, Ag, Au, In, Sn, Zn, Zr, Sc, Y, elements of the lanthanide series, alloys thereof, and mixtures thereof. Suitable alloy materials for use as the cathode layer include Ag—Mg, Al—Li, In—Mg, Al—Ca, and Al—Au alloys. Layered non-alloy structures may also be employed in the cathode, such as a thin layer of a metal such as calcium, or a metal fluoride, such as LiF, covered by a thicker layer of a metal, such as aluminum or silver. In particular, the cathode may be composed of a single metal, and especially of aluminum metal.

Polymers comprising structural units derived from compounds of formula I and II may be used in electron transport layers in place of, or in addition to traditional materials such as poly(9,9-dioctyl fluorene), tris(8-hydroxyquinolato) aluminum ($Alq_3$), 2,9-dimethyl-4,7-diphenyl-1,1-phenanthroline, 4,7-diphenyl-1,10-phenanthroline, 2-(4-biphenylyl)-5-(4-t-butylphenyl)-1,3,4-oxadiazole, 3-(4-biphenylyl)-4-phenyl-5-(4-t-butylphenyl)-1,2,4-triazole, 1,3,4-oxadiazole-containing polymers, 1,3,4-triazole-containing polymers, quinoxaline-containing polymers, and cyano-PPV.

Materials suitable for use in hole transporting layers include 1,1-bis((di-4-tolylamino) phenyl)cyclohexane, N,N'-bis(4-methylphenyl)-N,N'-bis(4-ethylphenyl)-(1,1'-(3,3'-dimethyl)biphenyl)-4,4'-diamine, tetrakis-(3-methylphenyl)-N,N,N',N'-2,5-phenylenediamine, phenyl-4-N,N-diphenylaminostyrene, p-(diethylamino) benzaldehyde diphenylhydrazone, triphenylamine, 1-phenyl-3-(p-(diethylamino)styryl)-5-(p-(diethylamino)phenyl)pyrazoline, 1,2-trans-bis(9H-carbazol-9-yl)cyclobutane, N,N,N',N'-tetrakis (4-methylphenyl)-(1,1'-biphenyl)-4,4'-diamine, copper phthalocyanine, polyvinylcarbazole, (phenylmethyl)polysilane; poly(3,4-ethylendioxythiophene) (PEDOT), polyaniline, polyvinylcarbazole, triaryldiamine, tetraphenyldiamine, aromatic tertiary amines, hydrazone derivatives, carbazole derivatives, triazole derivatives, imidazole derivatives, oxadiazole derivatives having an amino group, and polythiophenes as disclosed in U.S. Pat. No. 6,023,371

Materials suitable for use in the light emitting layer include electroluminescent polymers such as polyfluorenes, preferably poly(9,9-dioctyl fluorene) and copolymers thereof, such as poly(9,9'-dioctylfluorene-co-bis-N,N'-(4-butylphenyl) diphenylamine) (F8-TFB); poly(vinylcarbazole) and polyphenylenevinylene and their derivatives. In addition, the light emitting layer may include a blue, yellow, orange, green or red phosphorescent dye or metal complex, or a combination thereof. Materials suitable for use as the phosphorescent dye include, but are not limited to, tris(1-phenylisoquinoline) iridium (III) (red dye), tris(2-phenylpyridine) iridium (green dye) and Iridium (III) bis(2-(4,6-difluorephenyl)pyridinato-N,C2) (blue dye). Commercially available electrofluorescent and electrophosphorescent metal complexes from ADS (American Dyes Source, Inc.) may also be used. ADS green dyes include ADS060GE, ADS061GE, ADS063GE, and ADS066GE, ADS078GE, and ADS090GE. ADS blue dyes include ADS064BE, ADS065BE, and ADS070BE. ADS red dyes include ADS067RE, ADS068RE, ADS069RE, ADS075RE, ADS076RE, ADS067RE, and ADS077RE.

Organic compounds of formula I and II may form part of the electron transport layer or electron injection layer or light emissive layer. Thus, in one aspect, the present invention relates to more efficient optoelectronic devices, e.g., OLEDs comprising organic compounds of formula I and II. The OLEDs may be phosphorescent containing one or more, any or a combination of, blue, yellow, orange, green, red phosphorescent dyes.

DEFINITIONS

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), and anthraceneyl groups (n=3). The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehydes groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —$OPhC(CF_3)_2PhO$—), 4-chloromethylphen-1-yl, 3-trifluorovinyl-2-thienyl, 3-trichloromethylphen-1-yl (i.e., 3-$CCl_3$Ph-), 4-(3-bromoprop-1-yl)phen-1-yl (i.e., 4-$BrCH_2CH_2CH_2$Ph-), and the like. Further examples of aromatic radicals include 4-allyloxyphen-1-oxy, 4-aminophen-1-yl (i.e., 4-$H_2$NPh-), 3-aminocarbonylphen-1-yl (i.e., $NH_2$COPh-), 4-benzoylphen-1-yl, dicyanomethylidenebis(4-phen-1-yloxy) (i.e., —$OPhC(CN)_2PhO$—), 3-methylphen-1-yl, methylenebis(4-phen-1-yloxy) (i.e., —$OPhCH_2PhO$—), 2-ethylphen-1-yl, phenylethenyl, 3-formyl-2-thienyl, 2-hexyl-5-furanyl, hexamethylene-1,6-bis(4-phen-1-yloxy) (i.e., —$OPh(CH_2)_6PhO$—), 4-hydroxymethylphen-1-yl (i.e., 4-$HOCH_2$Ph-), 4-mercaptomethylphen-1-yl (i.e., 4-$HSCH_2$Ph-), 4-methylthiophen-1-yl (i.e., 4-$CH_3$SPh-), 3-methoxyphen-1-yl, 2-methoxycarbonylphen-1-yloxy (e.g. methyl salicyl), 2-nitromethylphen-1-yl (i.e., 2-$NO_2CH_2$Ph), 3-trimethylsilylphen-1-yl, 4-t-butyldimethylsilylphenl-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is an cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e., —$C_6H_{10}C(CF_3)_2C_6H_{10}$—), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g. $CH_3CHBrCH_2C_6H_{10}O$—), and the like. Further examples of cycloaliphatic radicals include 4-allyloxycyclohex-1-yl, 4-aminocyclohex-1-yl (i.e., $H_2C_6H_{10}$—), 4-aminocarbonylcyclopent-1-yl (i.e., $NH_2COO_5H_8$—), 4-acetyloxycyclohex-1-yl, 2,2-dicyanoisopropylidenebis(cyclohex-4-yloxy) (i.e., —$OC_6H_{10}C(CN)_2C_6H_{10}O$—), 3-methylcyclohex-1-yl, methylenebis(cyclohex-4-yloxy) (i.e., —$OC_6H_{10}CH_2C_6H_{10}O$—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —$OC_6H_{10}(CH_2)_6C_6H_{10}O$—), 4-hydroxymethylcyclohex-1-yl (i.e., 4-$HOCH_2C_6H_{10}$—), 4-mercaptomethylcyclohex-1-yl (i.e., 4-$HSCH_2C_6H_{10}$—), 4-methylthiocyclohex-1-yl (i.e., 4-$CH_3SC_6H_{10}$—), 4-methoxycyclohex-1-yl, 2-methoxycarbonylcyclohex-1-yloxy (2-$CH_3OCOC_6H_{10}O$—), 4-nitromethylcyclohex-1-yl (i.e., $NO_2CH_2C_6H_{10}$—), 3-trimethylsilylcyclohex-1-yl, 2-t-butyldimethylsilylcyclopent-1-yl, 4-trimethoxysilylethylcyclohex-1-yl (e.g. $(CH_3O)_3SiCH_2CH_2C_6H_{10}$—), 4-vinylcyclohexen-1-yl, vinylidenebis(cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl ($C_4H_7O$—) represents a $C_4$ cycloaliphatic radical. The cyclohexylmethyl radical ($C_6H_{11}CH_2$—) represents a $C_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" organic radicals substituted with a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g. —CH$_2$CHBrCH$_2$—), and the like. Further examples of aliphatic radicals include allyl, aminocarbonyl (i.e., —CONH$_2$), carbonyl, 2,2-dicyanoisopropylidene (i.e., —CH$_2$C(CN)$_2$CH$_2$—), methyl (i.e., —CH$_3$), methylene (i.e., —CH$_2$—), ethyl, ethylene, formyl (i.e.—CHO), hexyl, hexamethylene, hydroxymethyl (i.e. —CH$_2$OH), mercaptomethyl (i.e., —CH$_2$SH), methylthio (i.e., —SCH$_3$), methylthiomethyl (i.e., —CH$_2$SCH$_3$), methoxy, methoxycarbonyl (i.e., CH$_3$OCO—), nitromethyl (i.e., —CH$_2$NO$_2$), thiocarbonyl, trimethylsilyl (i.e., (CH$_3$)$_3$Si—), t-butyldimethylsilyl, 3-trimethyoxysilypropyl (i.e., (CH$_3$O)$_3$SiCH$_2$CH$_2$CH$_2$—)$_5$ vinyl, vinylidene, and the like. By way of further example, a C$_1$-C$_{10}$ aliphatic radical contains at least one but no more than 10 carbon atoms. A methyl group (i.e., CH$_3$—) is an example of a C$_1$ aliphatic radical. A decyl group (i.e., CH$_3$(CH$_2$)$_9$—) is an example of a C$_{10}$ aliphatic radical.

The term "heteroaryl" as used herein refers to aromatic or unsaturated rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as an ether, methylene or ethylene moiety. The common linking group may also be a carbonyl as in phenyl pyridyl ketone. As used herein, rings such as thiophene, pyridine, isoxazole, pyrazole, pyrrole, furan, etc. or benzo-fused analogues of these rings are defined by the term "heteroaryl."

The term "aryl" is used herein to refer to an aromatic substituent which may be a single aromatic ring or multiple aromatic rings which are fused together, linked covalently, or linked to a common group such as an ether, methylene or ethylene moiety. The aromatic ring(s) may include phenyl, naphthyl, anthracenyl, and biphenyl, among others. In particular embodiments, aryls have between 1 and 200 carbon atoms, between 1 and 50 carbon atoms or between 1 and 20 carbon atoms.

The term "alkyl" is used herein to refer to a branched or unbranched, saturated or unsaturated acyclic hydrocarbon radical. Suitable alkyl radicals include, for example, methyl, ethyl, n-propyl, i-propyl, 2-propenyl (or allyl), vinyl, n-butyl, t-butyl, i-butyl (or 2-methylpropyl), etc. In particular embodiments, alkyls have between 1 and 200 carbon atoms, between 1 and 50 carbon atoms or between 1 and 20 carbon atoms.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 50 carbon atoms or between 3 and 20 carbon atoms.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

EXAMPLES

Examples 1-7 describe the syntheses of compounds of formula II, polymers and intermediates used in making them. All reagents were purchased from Aldrich Chemical Co., Milwaukee, Wis., USA and Acros Organics unless other wise specified and were used without further purification. All compounds were characterized by $^1$H-NMR and found to correspond to the structures shown.

Example 1

Synthesis of Compound of Formula II

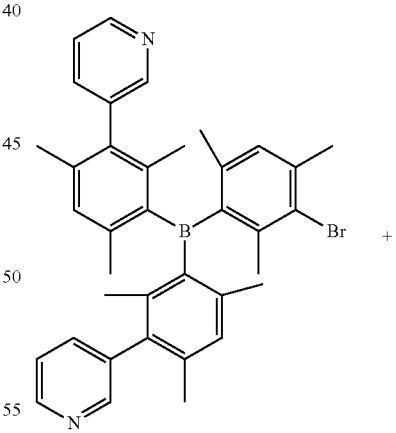

1

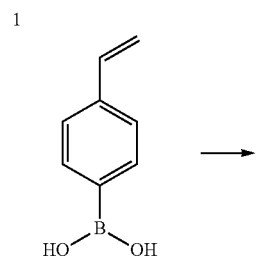

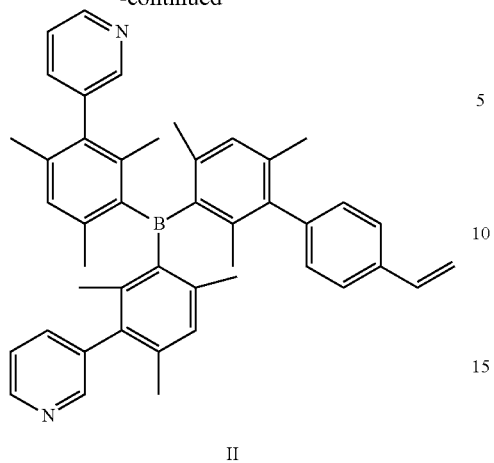

II

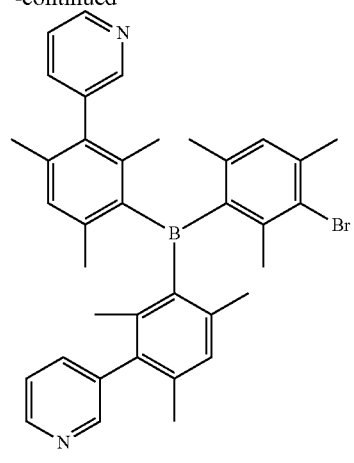

1

Mono-bromide precursor (Compound 1, 1.2 g, 2 mmol) and 4-phenylvinyl boronic acid (0.441 g, 3 mmol) were added into a 50 mL of 3-neck round bottom flask. To this flask, Pd(OAc)$_2$ (3.4 mg, 0.015 mmol), ligand 2-dicyclohexylphosphino-2',6'-dimethyoxybiphenyl (22 mg, 0.053 mmol) and 20 mL of toluene was added. This solution was degassed using a stream of argon for 15 min. In a separate vial, 3.7 g (5 mmol) of tetraethyl ammonium hydroxide (20% aq solution) and 3.7 g of water were combined and transferred to an additional funnel, degassed using a stream of nitrogen for 15 min. Then the base solution was gradually added to the toluene solution and the mixture was heated to 80° C. overnight under argon. The next day, after cooling to room temperature, the organic and aqueous layers were separated and methylene chloride was used to extract the aqueous layer twice. The organic layers were combined and extracted with water and brine solution. After dried over Na$_2$SO$_4$, the solution was concentrated to dryness and crude product was isolated using silica gel column with 40% EtOAC in Hexanes. $^1$H (CDCl$_3$, RT) 8.56 (m, 2H), 8.34 (m, 2H), 7.44-7.33 (m, 6H), 7.09-6.79 (m, 5H), 6.78-6.68 (m, 1H), 5.77 (dd, 1H), 5.24 (t, 1H), 2.4-1.62 (multiple multiplet, 27H).

Example 2

Synthesis of Compound 1

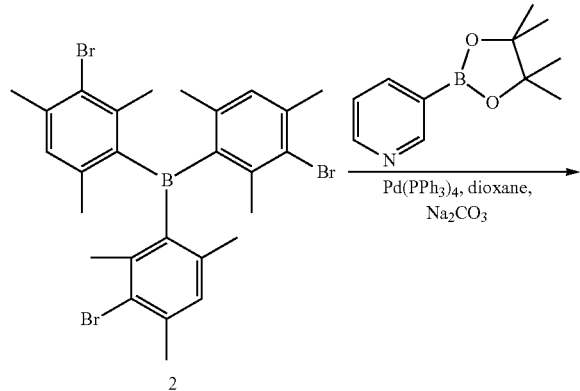

Tris(bromomesityl) borane (compound 2) (11.1 g., 18.4 mmol) and 7.57 g of 3-pyridylboronic acid pinacol ester (36.9 mmol) were added into 50 mL of dioxane along with 20 mL of Na$_2$CO$_3$ solution (2N). The reaction vessel was evacuated and purged with argon three times. Then 160 mg of Pd(PPh$_3$)$_4$ was added and the flask was evacuated and purged with argon three times. The reaction mixture was heated at 90° C. for 48 hours. After the reaction was cooled to room temperature, dioxane was removed by rotoevaporation. The residue was re-dissolved in CH$_2$Cl$_2$ (50 mL) and extracted with water (50 mL×2), brine (50 mL) and dried over anhydrous MgSO$_4$, and concentrated under reduced pressure. The crude product was further purified on silica gel using EtOAc/Hex (0-100%) as the eluting solvents. At 35%, 60% and 100% EtOAc, mono, di, tri adducts were collected respectively. $^1$H NMR for di-substituted product $^1$H (CDCl$_3$, RT) 8.56 (m, 2H), 8.34 (m, 2H), 7.45 (m, 2H), 7.34 (m, 2H), 6.90 (m, 3H), 2.4-1.62 (multiple multiplet, 27H).

Example 3

Synthesis of Compound 2

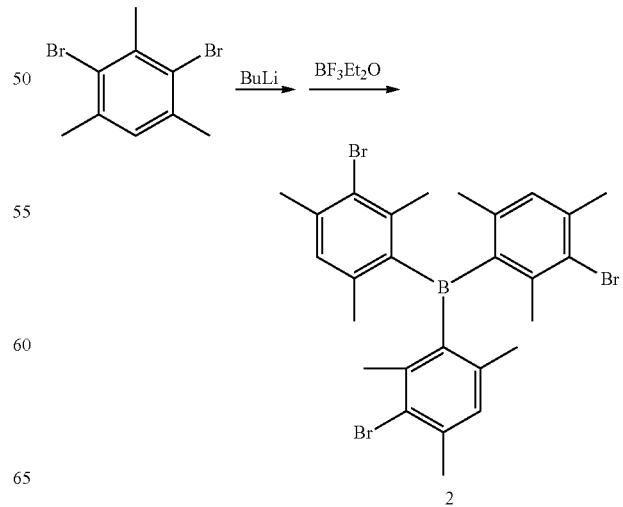

To a solution of 2,4-dibromomesitylene (13.9 g, 50 mmol) in dry Et$_2$O (400 mL) was added drop wise a hexane solution of n-BuLi (1.6 M, 31.25 mL, 50 mmol) at −78° C. The reaction mixture was allowed to warm to 0° C. and stirred for 20 min. To the mixture was added BF$_3$.OEt$_2$ (2.0 mL, 15.8 mmol) at −78° C. The reaction mixture was warmed up to room temperature over 1 h and stirred for overnight. After addition of water, the mixture was extracted with Et$_2$O. The extract was washed with brine, dried over anhydrous MgSO$_4$, and concentrated under reduced pressure to obtain a yellowish oil. The residue was dissolved in Et$_2$O and MeOH was added. Overnight, the solvent evaporated and crystals formed. The white crystals was collected by suction filtration and washed with MeOH to afford compound 2 (4.53 g, 47.7% yield). $^1$H (tetrachlorethane-d$_2$, 120° C.) 6.9 (s, 3H), 1.8 (s, 9H), 1.5 (s, 9H), 1.3 (s, 9H). $^1$H (tetrachlorethane-d$_2$, 30° C.), 6.9 (bs+s, 3H), 1.8 (s, 9H), 1.59 (d, 4.5H), 1.48 (d, 4.5H), 1.35 (d, 4.5H), 1.15 (d, 4.5H). $^{13}$C (tetrachlorethane-d$_2$, 120° C.) 146.2, 139.8, 139.7, 138.9, 131.0, 126.9, 24.4, 24.3, 24.4.

solution in hexane (1.56 mL, 2.5 mmol) in a drop wise fashion. The solution was stirred at 0° C. for 2 hours and then was warmed to room temperature. The solution was stirred overnight after an ether solution of compound 3 (1.1 g, 1.76 mmol) was added. Second day, the ether was removed and the residue was re-suspended into 10 mL of methylene chloride and 10 mL of water. Organic and aqueous layer was separated and methylene chloride was used to extract the aqueous layer twice. The organic layer was combined and extracted with water and brine solution. After dried over Na$_2$SO$_4$, the solution was concentrated to dryness and crude product was isolated using silica gel column with 40% EtOAC in Hexanes. $^1$H (CDCl$_3$, RT) 8.56 (m, 2H), 8.34 (m, 2H), 7.44-7.33 (m, 6H), 7.09-6.79 (m, 5H), 6.78-6.68 (m, 1H), 5.77 (dd, 1H), 5.24 (t, 1H), 2.4-1.62 (multiple multiplet, 27H).

Example 5

Synthesis of Compound 3

Example 4

Synthesis of Compound II

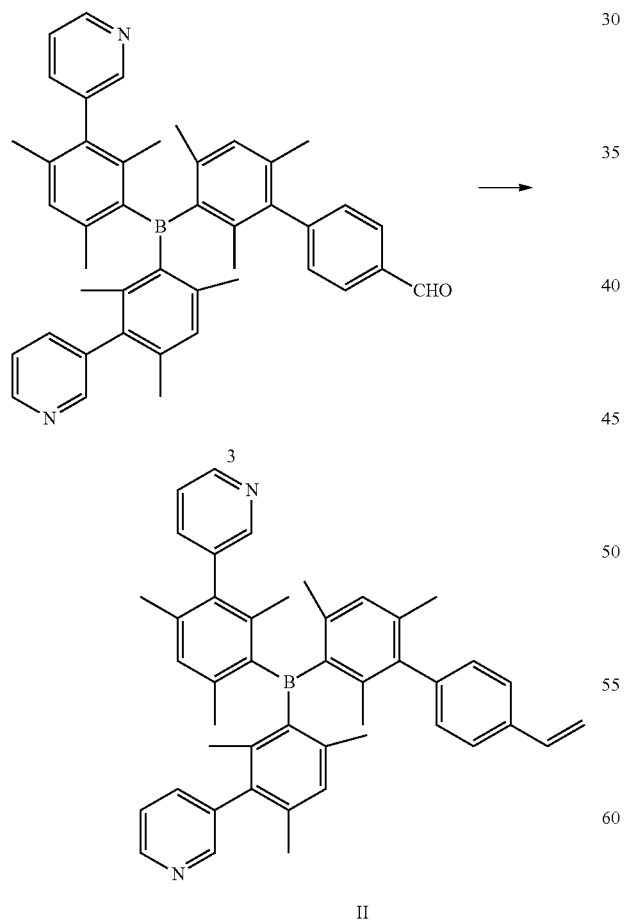

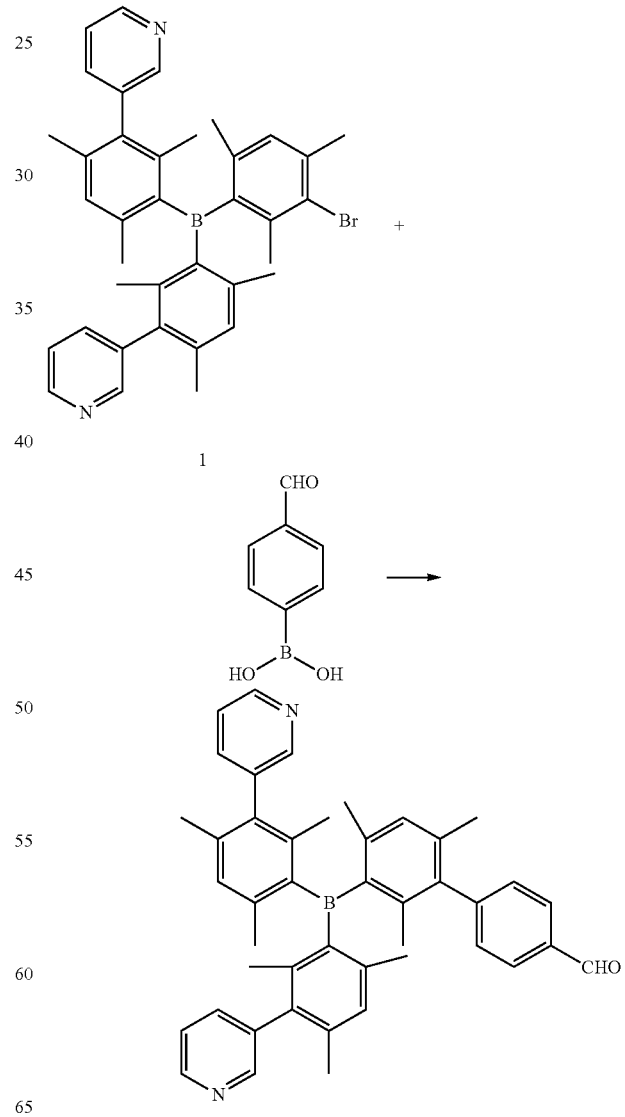

To a solution of methyltriphenylphosphonium bromide (927 mg, 2.6 mmol) in ether at 0° C. was added 1.6 M n-BuLi Mono-bromide precursor (compound 1, 1.21 g, 2 mmol) and 4-formylphenyl boronic acid (1.6 g, 10.6 mmol) were added into a 50 mL of 3-neck round bottom flask. To this flask, 20 mL of dioxane and 10 mL of $K_2CO_3$ (2N, aqueous solution) were added. This solution was degassed using a stream of argon for 15 min. Then a small pinch of $Pd(PPh_3)_4$ was added and the mixture was heated to 80° C. overnight under argon. The next day, after cooling to room temperature, the solvent was removed using roto-evaporation and the residue was re-suspended into 20 mL of methylene chloride and 20 mL of water. Organic and aqueous layer was separated and methylene chloride was used to extract the aqueous layer twice. The organic layer was combined and extracted with water and brine solution. After dried over $Na_2SO_4$, the solution was concentrated to dryness and crude product was isolated using silica gel column with 40% EtOAC in Hexanes. Maldi (M+): 626.3430

Example 6

Synthesis of Polymer

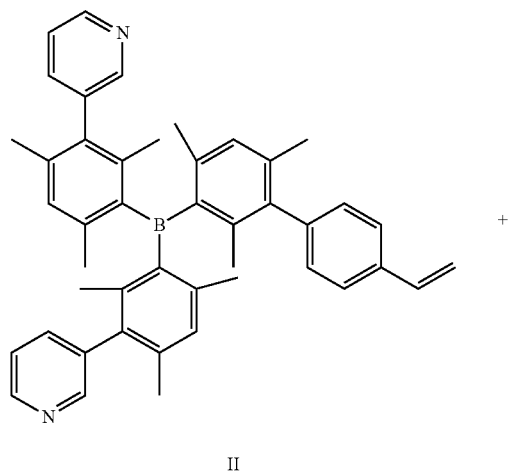

II

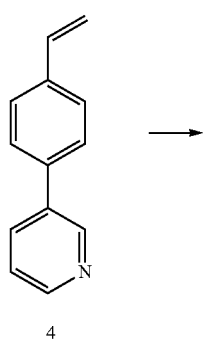

4

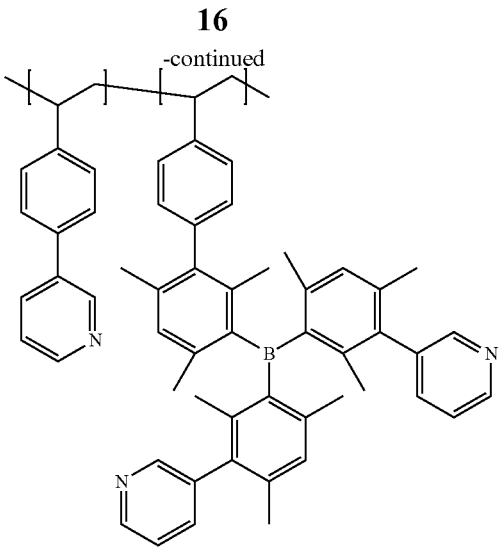

Vinyl monomer II (0.1252 g, 0.2 mmol) and vinyl phenyl pyridine (compound 4, 0.0036 g, 0.2 mmol) were added to a schlenk tube with 3 mL of NMP. AIBN in NMP (15 µl, 0.05 g/mL) was added via a syringe. The solution was evacuated using freeze-pump-thaw-cycle (3 times). The mixture was placed in an oil bath with temperature at 100° C. After 2 days, the reaction mixture was analyzed by GPC, using DMAC as the eluting solvent, Mw=33564, Mn=14852, PDI=2.2. The polymer was precipitated out into 10 mL of ether, and collected by centrifuge.

Example 7

Synthesis of Compound 4

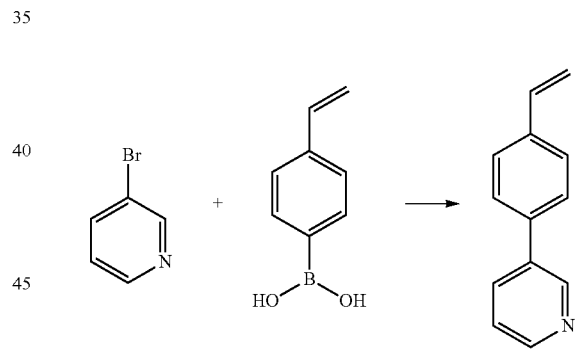

4-vinyl-phenyl boronic acid (10 g, 67.6 mmol), 3-bromopyridine (12.64 g, 0.08 mol), THF (100 mL), $K_2CO_3$ solution (14 g, 2 M) and water 100 mL were mixed together. The mixture was evacuated and filled with argon 3 times, then tetrakis(triphenylphosphine)palladium $(Pd(Ph_3)_4, 0.06$ g) was added. The mixture was degassed and filled with argon again. The mixture was stirred and heated to reflux overnight. After cooling to room temperature, water and THF were separated. Water layer was extracted with $CH_2Cl_2$ (10 mL) and combined with THF. Combined organic layer was evaporated and re-dissolved in $CH_2Cl_2$ (50 mL). Organic layer was extracted with water (50 mL×2) and brine (50 mL×1). After drying over $MgSO_4$. Solvent was removed in vacuo. After column chromatography on silica gel using EtOAc/hexanes as the eluting solvent, afforded 8 g of product. $^1H$ (CDCl$_3$) δ 8.9 (s, 1H), 8.62 (d, 1H), 7.92 (d, 1H), 7.56 (dd, 4H), 7.40 (d, 1H), 6.78 (dd, 1H), 5.83 (d, 1H), 5.34 (d, 1H).

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A compound of formula I:

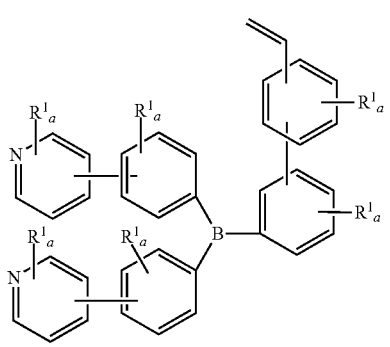

I wherein
- $R^1$ is independently at each occurrence a $C_1$-$C_{20}$ aliphatic radical, a $C_3$-$C_{20}$ aromatic radical, or a $C_3$-$C_{20}$ cycloaliphatic radical; and
- a is independently at each occurrence 0, or an integer ranging from 1 to 4.

2. The compound of claim 1, having chemical formula II

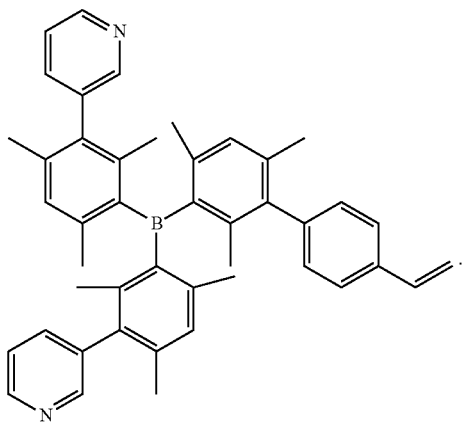

II

3. A polymer comprising structural units derived from a compound of formula I

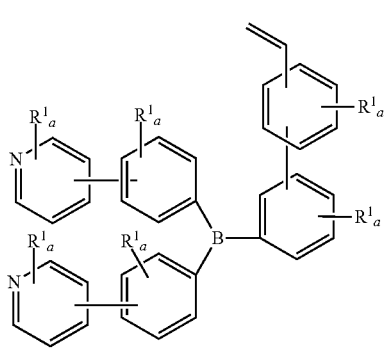

I wherein
- $R^1$ is independently at each occurrence a $C_1$-$C_{20}$ aliphatic radical, a $C_3$-$C_{20}$ aromatic radical, or a $C_3$-$C_{20}$ cycloaliphatic radical; and
- a is independently at each occurrence 0, or an integer ranging from 1 to 4.

4. The polymer of claim 3, additionally comprising structural units of formula

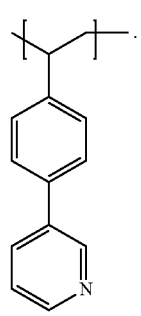

5. A polymer comprising structural units derived from a compound of formula II

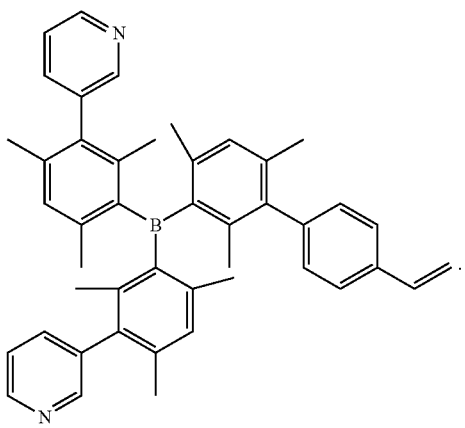

II

6. The polymer of claim 5, additionally comprising structural units of formula

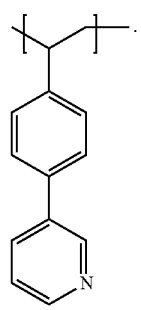

7. An optoelectronic device comprising a polymer comprising structural units derived from formula I

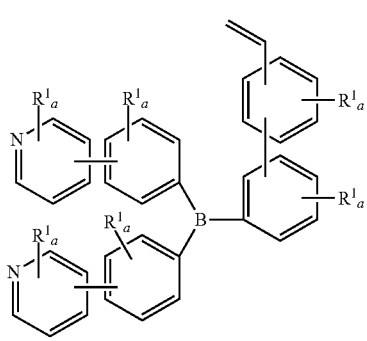

wherein
- $R^1$ is independently at each occurrence a $C_1$-$C_{20}$ aliphatic radical, a $C_3$-$C_{20}$ aromatic radical, or a $C_3$-$C_{20}$ cycloaliphatic radical; and
- a is independently at each occurrence 0, or an integer ranging from 1 to 4.

8. The optoelectronic device of claim 7, wherein the polymer additionally comprises structural units of formula

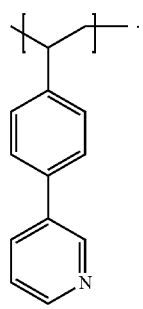

9. The optoelectronic device of claim 7, wherein the optical electronic device is a single layer OLED.

10. The optoelectronic device of claim 9, further comprising at least one blue, yellow, orange, green or red phosphorescent dye.

11. An optoelectronic device comprising a polymer having structural units derived from a compound of formula II

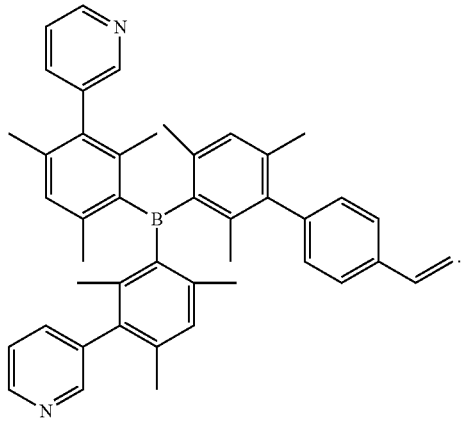

12. The optoelectronic device of claim 11, wherein the polymer additionally comprises structural units of formula

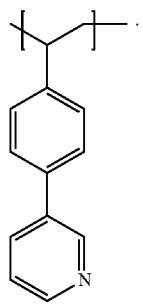

* * * * *

UNITED STATES PATENT AND TRADEMARK OFFICE
CERTIFICATE OF CORRECTION

PATENT NO. : 8,541,525 B2
APPLICATION NO. : 13/056539
DATED : September 24, 2013
INVENTOR(S) : Ye et al.

It is certified that error appears in the above-identified patent and that said Letters Patent is hereby corrected as shown below:

On the Title Page, in Item (57), under "ABSTRACT", in Column 2, Line 5,
delete "C1-C20" and insert -- $C_1$-$C_{20}$ --, therefor.

On the Title Page, in Item (57), under "ABSTRACT", in Column 2, Line 6,
delete "C3-C20" and insert -- $C_3$-$C_{20}$ --, therefor.

On the Title Page, in Item (57), under "ABSTRACT", in Column 2, Line 6,
delete "C3-C20" and insert -- $C_3$-$C_{20}$ --, therefor.

In the Specifications

In Column 2, Line 16, delete "same" and insert -- same. --, therefor.

In Column 6, Line 27, delete "U.S. Pat. No. 6,023,371" and insert -- U.S. Pat. No. 6,023,371. --, therefor.

In Column 7, Line 6, delete "anthraceneyl groups" and insert -- anthracenyl groups --, therefor.

In Column 8, Line 23, delete "(i.e., $H_2C_6H_{10}$-)," and insert -- (i.e., $H_2NC_6H_{10}$-), --, therefor.

In Column 8, Line 24, delete "(i.e., $NH_2COO_5H_8$-)," and insert -- (i.e., $NH_2COC_5H_8$-), --, therefor.

In Column 9, Line 23, delete "(i.e., $(CH_3O)_3SiCH_2CH_2CH_2$-)$_5$" and insert
-- (i.e., $(CH_3O)_3SiCH_2CH_2CH_2$-), --, therefor.

In Column 10, Line 26, delete "other wise" and insert -- otherwise --, therefor.

In Column 15, Line 19, delete "626.3430" and insert -- 626.3430. --, therefor.

Signed and Sealed this
Third Day of December, 2013

Margaret A. Focarino
*Commissioner for Patents of the United States Patent and Trademark Office*